United States Patent
Thers et al.

(10) Patent No.: US 12,157,015 B2
(45) Date of Patent: Dec. 3, 2024

(54) METHOD AND SYSTEM FOR MONITORING A HADRON BEAM DURING HADRON-THERAPY TREATMENT OF A SUBJECT

(71) Applicants: CENTRE NATIONAL DE LA RECHERCHE SCIENTIFIQUE, Paris (FR); INSTITUT MINES TÉLÉCOM, Paris (FR)

(72) Inventors: Dominique Thers, Treillières (FR); Jean-Sébastien Stutzmann, Orvault (FR)

(73) Assignees: CENTRE NATIONAL DE LA RECHERCHE SCIENTIFIQUE, Paris (FR); INSTITUT MINES TÉLÉCOM, Paris (FR)

( * ) Notice: Subject to any disclaimer, the term of this patent is extended or adjusted under 35 U.S.C. 154(b) by 0 days.

(21) Appl. No.: 17/769,039

(22) PCT Filed: Oct. 16, 2020

(86) PCT No.: PCT/FR2020/051863
§ 371 (c)(1),
(2) Date: Apr. 14, 2022

(87) PCT Pub. No.: WO2021/074551
PCT Pub. Date: Apr. 22, 2021

(65) Prior Publication Data
US 2024/0100365 A1  Mar. 28, 2024

(30) Foreign Application Priority Data
Oct. 18, 2019  (FR) ...................... 1911704

(51) Int. Cl.
*A61N 5/10*  (2006.01)

(52) U.S. Cl.
CPC ...... *A61N 5/107* (2013.01); *A61N 2005/1061* (2013.01)

(58) Field of Classification Search
CPC .... A61N 5/1049; A61N 5/107; A61N 5/1064; A61N 2005/1061; A61N 5/1067;
(Continued)

(56) References Cited

U.S. PATENT DOCUMENTS

2010/0265078 A1* 10/2010 Friedman .............. H01L 31/115
340/600

FOREIGN PATENT DOCUMENTS

| EP | 3305200 A1 | 4/2018 |
|----|------------|--------|
| WO | 2013036811 A1 | 3/2013 |
| WO | 2017156113 A1 | 9/2017 |

OTHER PUBLICATIONS

International Search Report mailed Dec. 23, 2020, in corresponding to International Application No. PCT/FR2020/051863; 9 pages (with English Translation).
(Continued)

*Primary Examiner* — Irakli Kiknadze
(74) *Attorney, Agent, or Firm* — Maier & Maier, PLLC

(57) ABSTRACT

A method for monitoring a hadron beam during hadron-therapy treatment of a subject including tumour cells labelled with a radiopharmaceutical product, in which the hadron beam includes a plurality of discrete hadron bursts, the method including the following steps: when a burst impacts on the subject, detecting the prompt gamma generated by the interaction of the hadrons of the burst with the tissues of the subject using a Compton telescope and reconstructing an image of the interaction volume; when no burst impacts on the subject, extracting the position of the tumour cells labelled with the radiopharmaceutical product using the Compton telescope and reconstructing an image of the total volume of the tumour; comparing the image of the interac-
(Continued)

tion volume and the image of the total volume of the tumour so as to locate the measured interaction volume relative to the measured total volume of the tumour.

15 Claims, 4 Drawing Sheets

(58) Field of Classification Search
CPC .......... A61N 5/1075; A61N 2005/1087; A61N 5/1001; A61N 5/1039; A61N 2005/1052; A61N 2005/1055; A61N 2005/1058; A61N 5/1077; A61N 5/1071; A61N 5/1048; A61N 5/1031; A61N 5/1028; A61N 2005/1097; A61N 2005/1022; A61N 2005/1092; A61N 2005/109; A61N 2005/1051; A61N 2005/1063; G01T 1/2935; G01T 3/008; G01T 1/185; G01T 1/18; G01T 1/2921; G01T 1/28; G01T 1/26; G01T 1/161; G01T 1/167; G01T 1/202; G01T 1/29; G01T 1/2985; G01T 1/2992; G01T 1/36; G01T 1/204; G01T 1/2018; H01J 47/002; H01J 47/02; H01J 47/08; C22C 19/05; H01L 31/115; A61B 6/4258; A61B 6/037; A61B 8/085; A61B 6/5205; A61B 6/032; A61B 5/4836; A61B 5/055; A61B 6/48; A61B 6/0478; A61B 6/5247; G01J 1/42
USPC .......................................................... 378/69
See application file for complete search history.

(56) References Cited

OTHER PUBLICATIONS

L. Gallego Manzano et al., "XEMIS: A liquid xenon detector for medical imaging"; Nuclear Instruments & Methods in Physics Research A; Elsevier; vol. 787; Nov. 20, 2014; XP029157774; pp. 89-93.

Katia Parodi, et al.; "On-and off-line monitoring of ion beam treatment"; Nuclear Instruments and Methods in Physics Research A; Elsevier; vol. 809; Jul. 6, 2015; XP029372104; pp. 113-119.

* cited by examiner

METHOD AND SYSTEM FOR MONITORING A HADRON BEAM DURING HADRON-THERAPY TREATMENT OF A SUBJECT

FIELD

The invention relates to a system and a method for monitoring a hadron beam during hadron-therapy treatment of a subject suffering from cancer. In particular, the invention relates to a system and a method for monitoring the interaction zone between the hadrons of the beam and the subject's tissues, and therefore indirectly the dose delivered, relative to the tumour mass to be treated which has been labelled with a radiopharmaceutical product comprising a radioisotope emitting a positron and a de-excitation gamma ray in quasi-coincidence.

BACKGROUND

Hadron-therapy is a highly effective cancer treatment which uses proton particle or carbon ion beams. This innovative technique has proven to be effective in the case of tumours that are difficult to treat using conventional radiotherapy as they are either radio-resistant, or located at a deep position or near vital organs. The use of hadron beams enables great precision in depositing the dose, both longitudinally and transversely. Indeed, unlike photon beams wherein the energy deposition is maximum from the first centimetres on entering the patient and abates with the depth, the charged ions deposit the energy maxima thereof at the end of the path thereof (Bragg peak) while maintaining a minimum input deposited dose. Moreover, the lateral penumbra of the protons is weaker than that obtained with a photon beam. However, the high ballistic precision of hadron-therapy makes this technique sensitive to any source of deviation relative to the treatment plan: poor patient positioning, organ movements or anatomical changes between fractions or tumour regression, weight loss, anatomical cavity filling between treatment sessions.

In order to exploit the advantage of the high ballistic precision, a thorough inspection of the location of the dose delivered by radiation is needed. When the primary beam stops inside the patient, the real-time monitoring of the path of the hadrons can be performed by means of secondary radiations, particularly gamma rays, from nuclear reactions of the hadrons in the body.

Some imaging regimens appear to be promising for obtaining information relating to the profile of the hadron beam, such as ion-induced ultrasound, secondary electron bremsstrahlung measurement or magnetic resonance imaging (MRI) which have specific problems associated with hadron beam deflection in the magnetic field in the case of real-time MRI. However, these techniques can be difficult to carry out. Currently, "in-beam" positron emission tomography (PET) systems have been proposed which use coincident gamma rays at 511 keV from the annihilation of positrons emitted during the beta decay of the radioactive isotopes generated by hadron interactions in tissues. However, due to the low number of isotopes undergoing beta decay, and given that the observation of beta decay is delayed, relative to the decay, by the duration of the lifetime of the radioactive isotopes, a relatively long data acquisition time is needed. Consequently, real-time beam imaging with in-beam PET only provides information relating to the position of the dose delivered after treatment. Furthermore, unlike conventional PET systems, the in-beam PET system has a reduced angle of coverage to enable the positioning of the "Gantry" isocentric rotary head, which reduces the sensitive volume of the system.

In this context, Frandes et al. (Frandes, Mirela, et al. "A tracking Compton-scattering imaging system for hadron therapy monitoring." IEEE Transactions on Nuclear Science 57.1 (2010): 144-150.) demonstrated, through digital simulations, the feasibility of a medical imaging system based on the combination of a Compton telescope and a pair-creation camera. Simulations of the system for different beam energies, typical of hadron-therapy, enabled Frandes et al. to demonstrate the ability of this imaging system to detect gamma rays in an energy regime characteristic of Compton interactions so as to reconstruct the position of the delivered dose. However, this system targeting the detection of gamma rays from annihilation, has the same drawback as in-beam PET.

Furthermore, the patient's internal anatomy can vary between one session and the next or during the same session. Consequently, being able to monitor the deposited dose position and quantity in the patient volume in real time is not sufficient to ensure that the target tumour volume is irradiated in its entirety while minimising the dose delivered to surrounding healthy tissue as much as possible. Indeed, a shift of the tumour volume relative to the external anatomical markers which are used to align the patient relative to the beam can have severe consequences in that the dose will not be delivered according to the treatment plan and therefore healthy tissue will be irradiated.

The invention is particularly intended to remedy these drawbacks by proposing a system enabling real-time monitoring during hadron-therapy treatment, both the position and the tumour mass and the position of the dose delivered by the beam in the patient enabling dose deposition in accordance with the treatment plan.

SUMMARY

The invention relates to a method for monitoring a hadron beam during hadron-therapy treatment of a subject comprising tumour cells labelled with a radiopharmaceutical product having a radioisotope emitting a positron and a de-excitation gamma ray in quasi-coincidence, wherein the hadron-therapy treatment is delivered according to a treatment plan comprising predefined parameters as a function of time in order to define at least one characteristic of the hadron beam over time during the hadron-therapy treatment, wherein the hadron beam comprises a plurality of discrete hadron "bursts" emitted at a predefined frequency by an acceleration device, the method comprising the following steps:
  when a "burst" impacts on the subject:
    detecting the "prompt gammas" generated by the interaction of the hadrons of the "burst" with the tissues of the subject by means of a liquid-xenon Compton telescope;
    using the "prompt gammas" detected to reconstruct an image of the interaction volume inside which the hadrons of the "burst" interact with the subject's tissues;
  when no "burst" impacts on the subject:
    extracting the position of the tumour cells labelled with the radiopharmaceutical product by simultaneously detecting the de-excitation gamma ray and two annihilation gamma rays produced by the positron by means of the liquid-xenon Compton telescope;

reconstructing an image of the total volume of the tumour to be treated by the hadron beam during the hadron-therapy treatment;

comparing the image of the interaction volume and the image of the total volume of the tumour so as to locate the measured interaction volume relative to the measured total volume of the tumour;

each time the measured interaction volume is at least partially included in the measured total volume of the tumour, computing the deviation between, on one hand, the position of the measured interaction volume in the measured total volume of the tumour and, on the other, a predefined position of the interaction volume in the total volume of the tumour defined in the treatment plan.

Thanks to the invention, it is possible to monitor a hadron-therapy treatment session in real time and effectively assess whether the treatment has been administered in accordance with the treatment plan thanks to the reconstruction and comparison of the image of the interaction volume and the image of the total volume of the tumour.

In one embodiment, the image of the interaction volume is obtained for each "burst" impacting on the subject. This makes it possible to monitoring the position of the beam in the subject in real time.

In one embodiment, the method further comprises a step wherein the deviation between the predefined position of the interaction volume and the position of the interaction volume measured relative to the measured total volume of the tumour is compared to a predefined threshold. Advantageously, this embodiment makes it possible to check in real time that the distribution of the dose delivered by the beam in the subject is in accordance, within an acceptable margin of error from a clinical point of view, with the treatment plan.

In one embodiment, each time the deviation is greater than the predefined threshold, the method comprises a step of computing at least one new parameter of the hadron beam so as to correct at least one characteristic of the hadron beam. A radiotherapy treatment plan is usually defined on the basis of a three-dimensional image of the subject obtained by "CT-scan" computed axial tomography by converting the Hounsfield units (HUs) into proton stopping power to be able to compute the dose distribution. However, the CT-scan is merely a static image of the subject in a given position and at a given time prior to the treatment. However, in hadron-therapy, organ movements, such as bowel movements, breathing, heartbeats or changes to the internal anatomy due to bladder filling or a weight variation, also give rise to changes in density, and therefore a modification of the length of the radiological path, along the beam trajectory. The influence thereof in proton-therapy can give rise to a severe under-dosage of the target clinical volume and an overdosage of organs at risk and normal tissues distal from the target. This embodiment makes it possible to account for any geometrical changes and to correct the parameters of the hadron beam in real time to make it possible to deliver the dose in the target tumour volume in the treatment plan.

In one embodiment, the subject is positioned on a motorised mechanical support configured to move the subject relative to the beam during the hadron-therapy treatment. In this embodiment, at least one of the predefined parameters of the treatment plan corresponds to the spatial position of the motorised mechanical support.

In one embodiment, each time the deviation is greater than the predefined threshold, the method comprises a step of computing the parameter of the treatment plan corresponding to a new spatial position of the motorised mechanical support so as to correct at least one characteristic of the hadron beam. This makes it possible to have the beam source in a fixed position and to avoid the use of a "Gantry".

In one embodiment, the new parameter of the hadron beam is sent to the acceleration device, which modifies at least one characteristic of the hadron beam so as to modify the position of the interaction volume relative to the measured total volume of the tumour. This creates a feedback loop enabling a real-time adjustment of the beam to the treatment plan.

In one embodiment, each time the deviation is greater than the predefined threshold, the method comprises stopping the hadron beam. Advantageously, this embodiment makes it possible to stop the treatment to prevent an overdosage of the organs at risk.

In one embodiment, the method further comprises a step of reconstructing a three-dimensional image sequence resulting from the merging of a three-dimensional image of the interaction volume with a three-dimensional image with the total tumour volume in the same Compton camera reference.

The invention also relates to a system for monitoring a hadron beam during hadron-therapy treatment of a subject comprising tumour cells labelled with a radiopharmaceutical product having a radioisotope emitting a positron and a de-excitation gamma ray in quasi-coincidence, wherein the hadron-therapy treatment is delivered according to a treatment plan comprising predefined parameters as a function of time in order to define at least one characteristic of the hadron beam over time during the hadron-therapy treatment, wherein the hadron beam comprises a plurality of discrete hadron "bursts" emitted at a predefined frequency by an acceleration device, the system comprising:

a beam imaging module configured to receive the data acquired from a liquid-xenon Compton telescope when a "burst" impacts on the subject and to analyse these data so as to determine the emission point of the "prompt gammas" generated by the interaction of the "burst" with the subject's tissues from which an image of the interaction volume inside which the hadrons of the "burst" interact with the tissues is reconstructed;

a tumour imaging module configured to receive the data acquired by the liquid-xenon Compton telescope when no "burst" impacts on the subject and to analyse these data so as to extract the position of the tumour cells labelled with the radiopharmaceutical product by simultaneously detecting the de-excitation gamma ray and two annihilation gamma rays produced by the positron and use the position of the tumour cells to reconstruct an image of the total volume of the tumour to be treated by the hadron beam during the hadron-therapy treatment;

an evaluation module configured to compare the image of the interaction volume and the image of the total tumour volume so as to locate the measured interaction volume relative to the measured total volume of the tumour and, each time the measured interaction volume is at least partially included in the measured total volume of the tumour, to compute the deviation between, on one hand, the position of the measured interaction volume relative to the measured total volume of the tumour and, on the other, a predefined position of the interaction volume within the total volume of the tumour defined in the treatment plan.

The system implementing the method according to the invention advantageously makes it possible to monitor in real time the dose delivered in the subject thanks to the reconstruction of the image of the interaction volume and the image of the total tumour volume, and to check that it complies with the dose distribution provided in the treatment plan.

In one embodiment, in the evaluation module, the image of the interaction volume is obtained for each burst impacting on the subject.

In one embodiment, the evaluation module is furthermore configured to compare the deviation between the predefined position of the interaction volume and the position of the interaction volume measured relative to the measured total volume of the tumour, to a predefined threshold.

In one embodiment, the subject is positioned on a motorised mechanical support configured to move the subject relative to the beam during the hadron-therapy treatment and wherein at least one of the predefined parameters of the treatment plan corresponds to the spatial position of the motorised mechanical support.

According to one embodiment, the system further comprises a correction module configured to compute at least one new parameter of the hadron beam, each time the deviation is greater than the predefined threshold, in order to correct at least one characteristic of the hadron beam.

According to one advantageous feature, the correction module is furthermore configured to send the new parameter of the hadron beam to the acceleration device, which modifies at least one characteristic of the hadron beam so as to modify the position of the interaction volume relative to the measured total volume of the tumour.

According to one embodiment, the system further comprises a safety module configured to send the acceleration device the instruction to stop the hadron beam each time the deviation is greater than the predefined threshold.

According to one embodiment, the system further comprises an image reconstruction module configured to reconstruct a three-dimensional image sequence resulting from the merging of a three-dimensional image of the interaction volume with a three-dimensional image with the total tumour volume according the same Compton camera reference.

According to one embodiment, the system comprises the Compton telescope, being a liquid-xenon Compton telescope.

According to one embodiment, the system comprises the acceleration device and/or the motorised mechanical support.

According to one embodiment, the method for monitoring a hadron beam is a computer-implemented method.

The invention also relates to a computer program comprising instructions which, when the program is run by a computer, result in the latter implementing the method for monitoring a hadron beam described above.

The invention also relates to a computer-readable recording medium comprising instructions which, when they are run by a computer, result in the latter implementing the method for monitoring a hadron beam described above.

Definitions

In the present invention, the terms below are defined as follows:
"Burst" refers to a bunch of hadrons having the same acceleration phase.
"Prompt Gammas" refers to high-speed and high-energy gamma rays which are naturally emitted following nuclear reactions of the hadrons with the subject's tissues.
"Organs At Risk (OARs)" refers to organs on which the physician sets dose constraints not to be exceeded in order to prevent irradiation-related side-effects as much as possible.
"PTV (or Planning Target Volume)", refers to a volume, which includes the tumour visible in imaging investigations (GTV or "Gross Tumour Volume") extended by therapeutic margins defined by the physician according to the type of disease treated (CTV or "Clinical Target Volume"), by adding a margin defined by the imprecisions due to the treatment process (uncertainties in respect of path, positioning, intrinsic uncertainties of treatment machine, etc.).
"Subject" refers to a mammal, preferably a human According to the present invention, a subject can be a patient, i.e. a person under medical supervision, undergoing or having undergone a medical treatment, or undergoing follow-up for the development of a disease.

BRIEF DESCRIPTION OF THE DRAWINGS

The features and advantages of the invention will emerge in the following description of several embodiments of a system and a method according to the invention, given merely by way of non-limiting example and referring to the appended drawings wherein.

DETAILED DESCRIPTION

Figure 1:
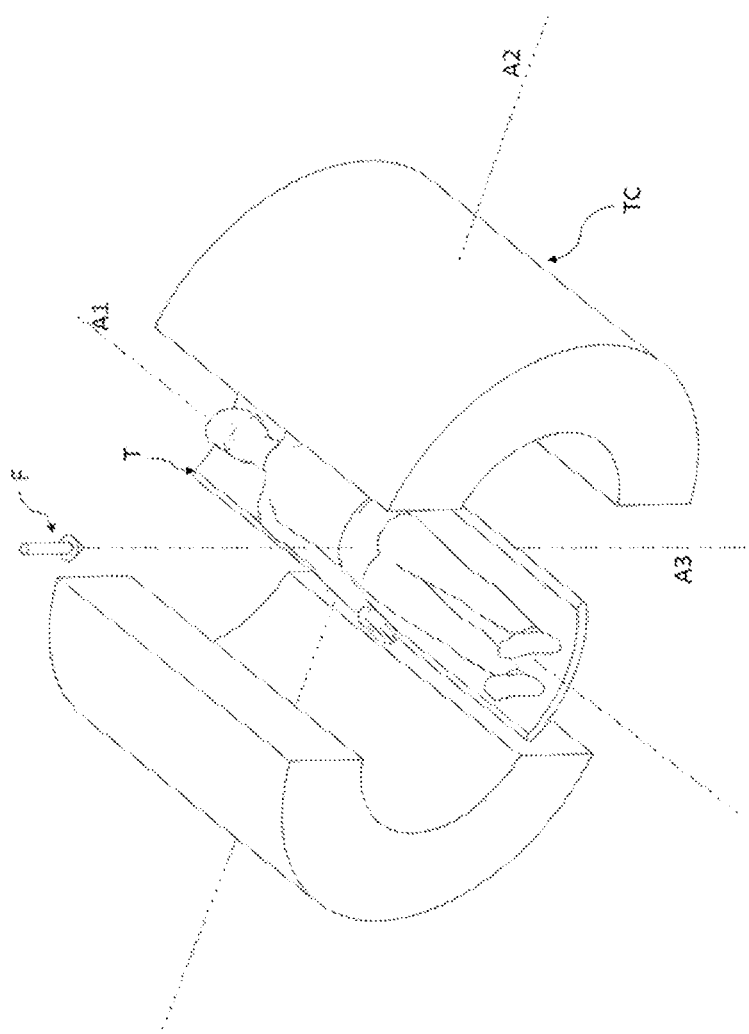
FIG. 1 is a schematic perspective view of a treatment table and the open-configuration Compton telescope, according to a first embodiment of the invention.

The present invention relates to a method for monitoring a hadron beam during hadron-therapy treatment of a subject suffering from a tumour.

Typically, in a hadron-therapy centre, the hadrons are accelerated at therapeutic energies, between 70 and 250 MeV, generally with a cyclotron or a synchrotron, and are transported into the treatment room where they enter a treatment nozzle. The thin initial hadron beams are distributed laterally and longitudinally and suitably formatted to enable treatments. The hadrons used are typically protons or carbon ions. The scattering and formatting of the beam can be carried out using electromechanical means for treating patients with passively-scattered hadron-therapy (PSHT). This technique is particularly used with the proton. A second mode, referred to as uniform scanning, consists of scanning a rough beam over a wide field which is then collimated and compensated in depth by accessories customised for the patient's anatomy. This makes it possible to treat wider fields with deeper paths. Another approach consists of magnetic scanning of mini-beams of hadrons at an initial energy sequence. The hadrons are scanned very finely and precisely in the tumour in the three directions (x,y,z) in order to irradiate the latter without using customised accessories. This technique can be used to treat patients with intensity modulated hadron-therapy.

Said hadron-therapy is delivered according to a treatment plan comprising predefined parameters as a function of time in order to define at least one characteristic of the hadron beam over time during the hadron-therapy treatment.

According to an embodiment, the predefined parameters which define at least one characteristic of the beam vary according to the hadron-therapy technique used.

For the passive scattering method, the lateral and longitudinal scattering of the beam is obtained thanks to the use of a path modulation wheel and one or two scatterers made of high-Z materials to produce a flat wide beam in the region of interest. The modulation wheel is configured to insert blades of different thicknesses of material on the path of the hadrons during the rotation thereof to spread the Bragg peak and adjust it to the depth of the target volume. The modulation of the Bragg peak is therefore discrete. The blade thicknesses and widths are designed such that the sum of the resulting individual Bragg peaks gives a dose distribution of uniform and homogeneous depth, SOBP or "spread-out Bragg peak". To adapt the dose distribution laterally to the shape of the target volume (plus suitable margins), an aperture, generally consisting of brass blocks of sufficient thickness (2 cm to 8 cm) to absorb the highest-energy incident hadrons, is used. Finally, to create a dose distribution according to the distal shape of the target, the Bragg peak of the passively scattered beam is spread out farther using a distance compensator.

According to one embodiment, the hadron-therapy treatment uses the passive scattering technique. In this embodiment, the predefined parameters comprise at least the beam energy and the hadron path modulation (i.e. SOBP). Indeed, the absorber and the compensator are accessories customised for the patient and the position thereof does not change during treatment.

For uniform scanning, an active scanning system is used, which, with multiple mini-irradiations, constructs a Bragg peak modulated in the tumour. The target volume is irradiated by lateral scanning of one layer after another. A dedicated modulation wheel is used to translate the Bragg peaks step by step. For a better definition of the modulated Bragg peak, intermediate-depth layers are irradiated thanks to the association of the absorber plates of a scatterer and the blades of the modulation wheel. Once modulated, the proton beam is then widely scanned in the Y and X directions respectively by a vertical magnet in the first position then by a horizontal magnet which follows.

According to one embodiment, the hadron-therapy treatment uses the uniform scanning technique. In this embodiment, the predefined parameters comprise at least the beam energy, the hadron path modulation and the X and Y position of the beam.

Active mini-beam scanning consists of scanning an elementary ion beam precisely with magnets horizontally and vertically while changing the initial energy of the protons in order to scan layer by layer the entire tumour volume without using accessories customised to the patient. The depth (Z) is managed by the proton beam energy modulation thanks to the energy selection system. The position of the fine beam in the plane (X, Y) is controlled thanks to the same scanning magnets as described hereinafter. A set of spots is thus created and distributed over the entire target volume. The size of the spot at the isocentre is adapted thanks to the quadrupoles located before the scanning magnets. The main advantage thereof is that of reducing the quantity of neutrons produced and the output loss, both due to the passive beam formatting accessories.

According to one embodiment, the hadron-therapy treatment uses the active mini-beam scanning technique. In this embodiment, the predefined parameter comprises at least the X, Y and Z coordinates (i.e. the beam energy) and the intensity of each spot.

The techniques implementing magnetic beam scanning can be configured to enable a beam deflection making it possible to cover a treatment field capable of attaining 30 cm×40 cm.

In a hadron-therapy treatment room, the subject is normally sitting on a chair or reclined on a treatment table in a predefined position relative to the treatment nozzle, from which the beam emerges to impact on the subject.

In one embodiment, the treatment nozzle is located in a fixed position at a predefined distance from the subject. The treatment nozzle can be positioned relative to the subject such that the direction of incidence of the beam F enters the subject perpendicularly to the sagittal plane of the subject. In a preferred embodiment, the treatment nozzle is positioned facing the subject such that the beam has the point of entry thereof on the anterior part of the subject. This enables the beam to penetrate the subject up to the target volume by passing through the smallest possible thickness of healthy tissues and/or organs at risk, so as to reduce the dose that they receive.

With a treatment nozzle in a fixed position, the direction of incidence of the beam F, and therefore also the point of entry thereof in the tissues, can be varied merely using the magnetic scanning, which enables small-scale deviations of the beam.

To make it possible to vary the angle of incidence of the beam over an arc of more than 180 degrees, in an embodiment, the treatment table T is configured to move the subject relative to the point of incidence of the beam, particularly during the hadron-therapy treatment. In this first embodiment illustrated in FIG. 1, the treatment table T is capable of rotating about the three axes A1, A2 and A3 in both directions of rotation and of translating along the axes A1, A2 and A3 in both opposite directions of each axis.

In this first embodiment, the Compton telescope TC comprises two Compton semi-detectors in the form of two hollow half-cylinders, symmetrical relative to the axis A1 and separated from one another along the direction A2 so as to enable the passage of a beam F arriving above the subject. The two half-cylinders are complementary and capable of forming a full hollow cylinder if joined. Particularly, each semi-detector forms an arc of a circle having an angle 180°. In this embodiment, each Compton semi-detector is capable of translating along the axes A1, A2 and A3 in both directions and rotating about the axis A3.

Figure 3:
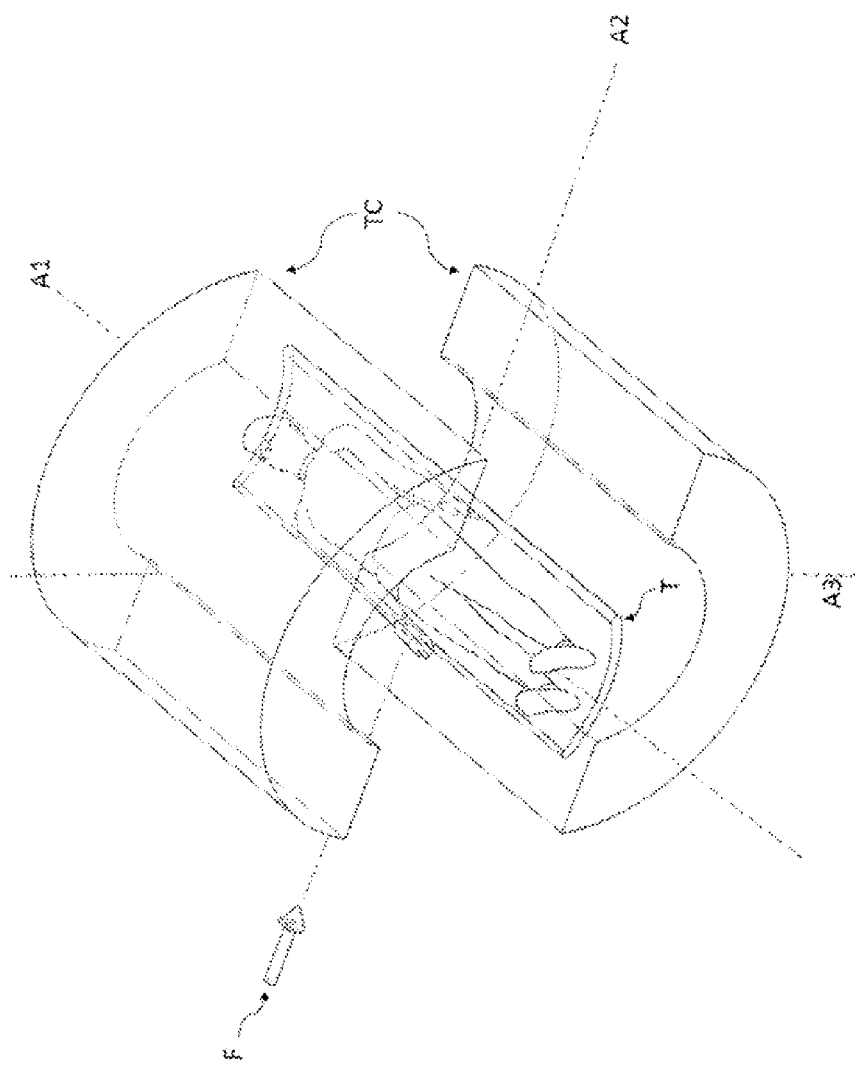
FIG. 3 is a schematic perspective view of a treatment table and an open-configuration Compton telescope, according to a second embodiment of the invention.

In the second embodiment illustrated in FIG. 3, the treatment table T is also capable of rotating about the three axes A1, A2 and A3 in both directions of rotation and of translating along the axes A1, A2 and A3 in both opposite directions of each axis. The Compton telescope TC comprises two Compton semi-detectors in the form of two hollow half-cylinders, symmetrical relative to the axis A1 and separated from one another along the direction A3 so as to enable the passage of a beam F arriving on the subject's side.

The configuration of the Compton telescope in the first and second embodiments is referred to in the present description as "open-configuration Compton telescope". In the first and second embodiments, each Compton semi-detector can be moved independently from each other to adapt more to the position and direction of incidence of the beam F on the subject while retaining the most closed configuration possible of the Compton telescope TC on the subject. Indeed, the Compton telescope has a higher spatial resolution when the two semi-detectors are closest to the subject enabling the detection of a greater number of events (i.e. prompt gammas, de-excitation gamma ray or annihilation gamma).

Figure 4:
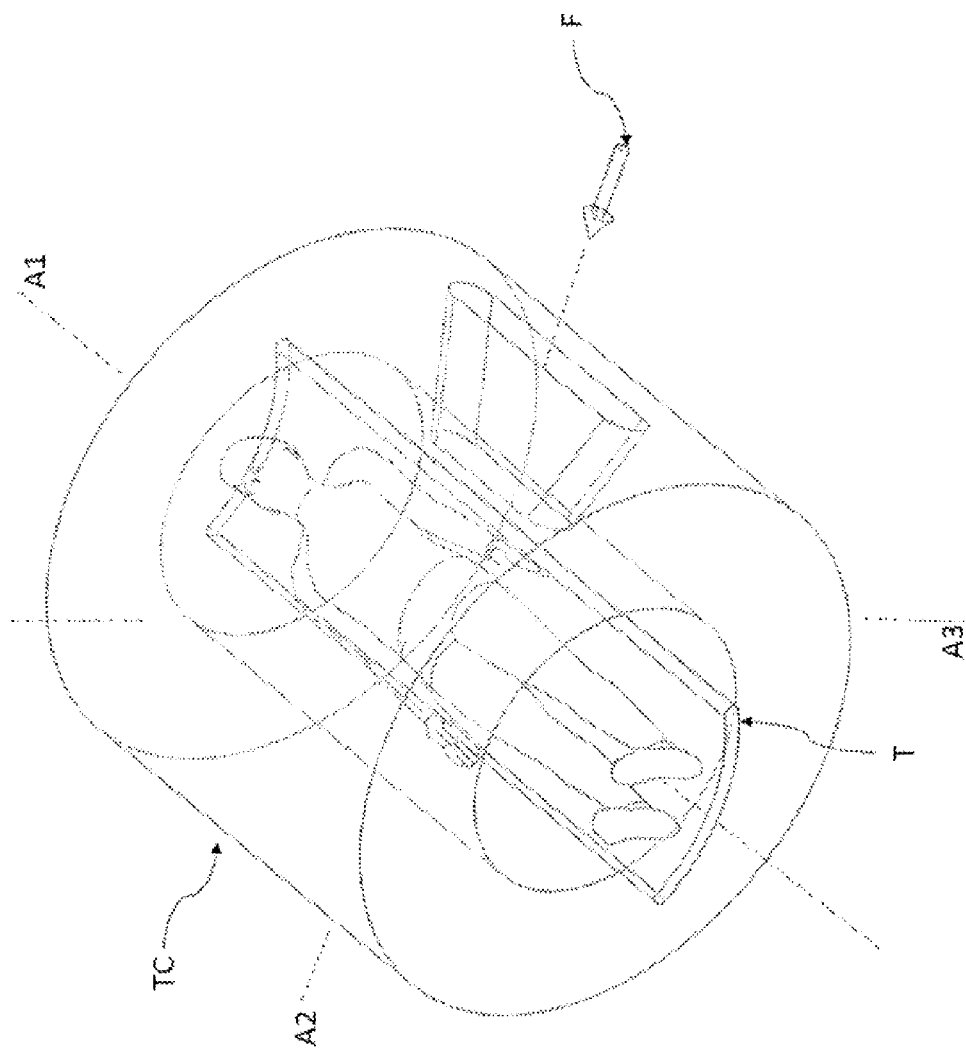
FIG. 4 is a schematic perspective view of a treatment table and a closed-configuration Compton telescope, according to a third embodiment of the invention.

In the third embodiment illustrated in FIG. 4, the Compton telescope comprises a single detection volume having the form of a hollow cylinder and comprising a lateral slit having dimensions capable of allowing the passage of a beam F arriving on the subject's side. This configuration of the Compton telescope is referred to in the present description as "closed-configuration Compton telescope". The treatment table T aligned along the axis A1, being also the longitudinal axis of a hollow cylinder. The treatment table T is capable of being moved inside the closed-configuration Compton telescope and particularly of rotating about the three axes A1, A2 and A3 in both directions of rotation and of translating along the axes A1, A2 and A3 in both opposite directions of each axis. In this embodiment, the Compton telescope is mounted on a mechanical support, motorised so as to be able to translate along the axes A1, A2 and A3 and to pivot about the axis A3.

In the first, second and third embodiments, the treatment table T whereon the subject is positioned is solidly mounted on a motorised mechanical support (not shown) which enables it to move with the degrees of freedom described hereinafter. The motorised mechanical support is particularly capable of enabling rotating movements of the treatment table T with an interval which varies between 2 and 15 degrees and translation movements by an interval which varies between 0.5 cm and 5 cm.

In an embodiment, the motorised support is a robotic positioning arm configured to have a sensitivity between 0.1 cm and 1 cm.

In the embodiments comprising a treatment table T on a motorised mechanical support, at least one of the predefined parameters of the treatment plan corresponds to the spatial position of the treatment table T and therefore of the motorised mechanical support. This particularly advantageous embodiment makes it possible to avoid the use of huge isocentric rotary heads ("Gantry") configured to deliver the beam with a variable angle over more than 180°. The "Gantry", wherein the treatment nozzle is incorporated, has an extremely high production cost compared to that of a motorised treatment bed. Consequently, avoiding the use of the "Gantry" makes it possible to reduce the construction cost of hadron-therapy infrastructures rendering this technique more accessible.

In the embodiments wherein the Compton telescope is capable of being moved, at least one of the predefined parameters of the treatment plan corresponds to the spatial position of the closed-configuration Compton telescope or of each Compton semi-detector of the open-configuration Compton telescope.

The acceleration device used in the method according to the present invention produces a hadron beam comprising a plurality of discrete hadron "bursts" emitted at a predefined frequency by an acceleration device.

In one embodiment, the acceleration device which generates the hadron beam used is a synchrotron or a linear accelerator. Synchrotrons accelerate hadrons at the desired energy in bunches (pulses). Once a bunch has reached the required energy, it is extracted and sent via the "beam line" to the treatment room. However, regardless of the type of accelerator, the narrow monoenergetic beam extracted is guided magnetically through the beam line to the treatment nozzle.

In one embodiment, the acceleration device is a "digital" synchrotron comprising induction cells wherein the magnets are exposed to rapid variations of the operation thereof thanks to external beam control means and onboard computers capable of controlling them (switch and FPGA).

The interaction of a "burst" produces in the material, in addition to the self-activation and emission of charged particles, rapid emission of high-energy gamma rays referred to as "prompt gammas". The "prompt gamma" generation profile is well correlated with the hadron path. Consequently, the detection of "prompt gammas" can be used effectively to monitor the interaction point of the beam and the dose deposition in the subject.

Figure 2:
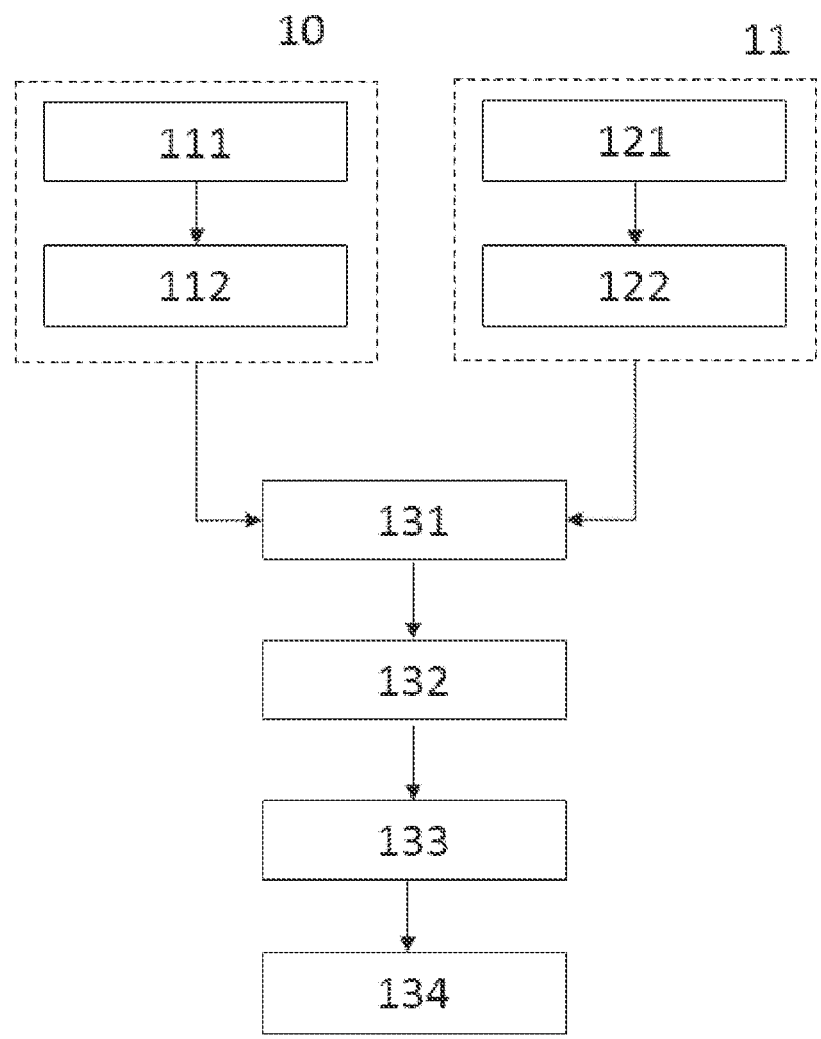
FIG. 2 is a flow chart representing the steps of the method according to a first embodiment of the invention.

FIG. 2 illustrates an embodiment of the method comprising several data acquisition and computing steps.

The method according to the present invention is configured to enable the real-time monitoring of a hadron-therapy treatment by obtaining sequences of images of the interaction volume inside which the hadrons of the "burst" interact with the subject's tissues and of the total tumour volume. The image of the interaction volume can be obtained only while a "burst" impacts on the subject.

The method therefore comprises a first phase, when a "burst" impacts on the subject 10, this first phase comprising the following steps:
  detecting the "prompt gammas" 111 generated by the interaction of the hadrons of the "burst" with the tissues of the subject by means of a Compton telescope;
  using the "prompt gammas" detected to reconstruct an image 112 of the interaction volume inside which the hadrons of the "burst" interact with the subject's tissues.

In a preferred embodiment, the Compton telescope is a liquid-xenon Compton telescope. The fundamental physical properties of liquid xenon, such as the high density thereof and the high atomic number thereof, give the ionising radiation a high stopping power, which makes liquid xenon an ideal material as a gamma ray detector in the energy range from a few dozen keV to several dozen MeV. Liquid xenon is both an excellent active medium for detecting ionising radiation and an excellent scintillator, with the advantage of enabling the construction of large-sized detectors with a homogeneous sensitive medium. A Compton telescope uses successive interactions (two or more) of an incident photon in the interaction volume. Based on the interaction points and the energy deposited at each interaction, the direction of the incident photon can be reduced to a cone, via the application of Compton kinematics. The position of the photon source can be determined by the intersection of different Compton cones, inferred from the subsequent interactions of photons from the same source. This type of detector is therefore well adapted for detecting "prompt gammas" in the corresponding energy range of several MeV wherein Compton scattering is the dominant process.

The image of the measured interaction volume can be a three-dimensional image.

In one embodiment, the image of the interaction volume is obtained for each "burst" impacting on the subject. In this embodiment, the image acquisition frequency is dependent on the "burst" production frequency in the acceleration device. The image number acquired per second can therefore vary from 5 to 30.

In one embodiment, the Compton telescope is configured to have a spatial resolution of approximately 1 mm for each image of a "burst".

In the present invention, the subject's tumour cells are labelled with a radiopharmaceutical product comprising a radioisotope emitting a positron and a de-excitation gamma ray in quasi-coincidence. This enables the identification of the position of the radio-marker thanks to the use of the three-photon imaging principle. Indeed, the positron travels along a short path in the tissues (of the order of one mm) before annihilating in two photons at 511 keV moving in the opposite direction ("back-to-back gammas").

Three-photon imaging is based on the combined use of a Compton telescope and a radiopharmaceutical having a radioisotope emitting a positron and a de-excitation gamma ray in quasi-coincidence.

The simultaneous detection of these two annihilation photons makes it possible to plot the line of response (LOR), i.e. a line connecting the two interaction points of the annihilation photons in the Compton telescope and passing through the annihilation point of the positron in the tissue. The position of the radioisotope is therefore obtained by the intersection between LOR and the Compton cone defined based on the interaction of the de-excitation gamma with the Compton telescope. The surface of the Compton cone comprises the incident direction of the de-excitation gamma and can be directly inferred from the Compton kinematics. The angle of aperture of the Compton cone, θ, is defined by the Compton scattering formula, wherein the axis of the Compton cone is determined using the first of the two interaction points of the de-excitation gamma entering the telescope.

This technique advantageously enables a reduction in the number of decays required to obtain the image and therefore to reduce the acquisition time and/or the quantity of substance inoculated per patient.

The first phase of the method comprises, when no "burst" impacts on the subject 11, the following steps:—
- extracting the position of the tumour cells 121 labelled with the radiopharmaceutical product by simultaneously detecting the de-excitation gamma ray and two annihilation gamma rays produced by the positron by means of the Compton telescope, as described above;
- reconstructing, based on positions of the tumour cells, an image of the total volume of the tumour 122 to be treated by the hadron beam during the hadron-therapy treatment.

In one preferred embodiment, the radioisotope used in the radiopharmaceutical is $^{44}$Sc, which emits a positron and a photon of energy 1.157 MeV in spatial and temporal quasi-coincidence.

The image of the total tumour volume is acquired between two successive "bursts" to prevent contamination of the image by the signal generated by the "prompt gammas".

In one example, the structure of the Compton telescope is such that for an acquisition of 10 s, the spatial resolution of the image of the total volume of the tumour is approximately 1 mm The resolution attained is due to the physical limitations of the detector and to the activity of the isotope injected into the subject.

In one embodiment, the image of the total volume of the tumour is a three-dimensional image.

The method further comprises a second phase comprising the following phases:
- comparing the image of the interaction volume and the image of the total volume of the tumour 131 so as to locate the measured interaction volume relative to the measured total volume of the tumour;
- each time the measured interaction volume is at least partially included in the measured total volume of the tumour, computing the deviation 132 between, on one hand, the position of the measured interaction volume in the measured total volume of the tumour and, on the other, a predefined position of the interaction volume in the total volume of the tumour defined in the treatment plan.

The deviation can be computed by superimposing the images. This is easy to obtain, once the images of the measured interaction volume and of the measured total tumour volume are acquired by the same detector and are therefore reconstructed relative to the same reference.

The comparison phase makes it possible to compare the actual position of the Bragg peak relative to the position computed in a computing software for generating the treatment plan.

In one embodiment, the method further comprises a step 133 wherein the deviation between the predefined position of the interaction volume and the position of the interaction volume measured relative to the measured total volume of the tumour is compared to a predefined threshold. The predefined threshold can correspond to a margin of 1 mm to 5 mm around the target volume (PTV). The threshold can also be defined on the basis of the radiosensitivity of the organs at risk which surrounds the target volume. For example, the predefined threshold corresponds to a margin of 0.5 mm towards the lymph nodes which are highly radiosensitive and margin of 1 mm in the direction of the lungs which are less so.

In one embodiment, each time the deviation is greater than the predefined threshold, the method comprises a step of computing at least one new parameter of the hadron beam 134 so as to correct at least one characteristic of the hadron beam.

In one embodiment, each time the deviation is greater than the predefined threshold, the method comprises a step of computing the parameter of the treatment plan corresponding to a new spatial position of the motorised mechanical support so as to correct at least one characteristic of the hadron beam.

In one embodiment, the new parameter of the hadron beam is sent to the acceleration device which modifies at least one characteristic of the hadron beam so as to modify the position of the interaction volume relative to the measured total volume of the tumour.

In one embodiment, each time the deviation is greater than the predefined threshold, the method comprises stopping the hadron beam. This makes it possible to have a safety measure to avoid any irradiation not in accordance with the treatment plan.

In one embodiment, the method further comprises a step of reconstructing a three-dimensional image sequence resulting from the merging of a three-dimensional image of the interaction volume with a three-dimensional image with the total tumour volume in the same Compton camera reference. Such an image sequence can be viewed in real-time thanks to a screen to provide the medical profession with visual information.

The invention also relates to a system for monitoring a hadron beam during a hadron-therapy treatment of a subject. The system is configured to monitor a hadron beam, comprising a plurality of discrete hadron "bursts" emitted at a predefined frequency by an acceleration device, during a hadron-therapy treatment delivered according to a treatment plan comprising predefined parameters as a function of time in order to define at least one characteristic of the hadron beam over time during the hadron-therapy treatment.

The system for monitoring a hadron beam will now be detailed. Hereinafter, the modules should be understood as functional entities rather than as physically separate hardware components. Therefore, they can either be grouped in the same concrete hardware component, or distributed into several of these components. Furthermore, each of these modules is optionally in turn shared between at least two physical components. Furthermore, the modules are implemented in hardware, software, microprograms or any other combined form thereof.

The system comprises a beam imaging module configured to receive data acquired from a Compton telescope when a "burst" impacts on the subject. In an embodiment, the data acquisition is performed on-line and continuously. The data acquired during a time window, corresponding to the dispatch of a "burst" to a subject, are sent to the beam imaging module. This module is furthermore configured to analyse these data so as to determine the emission point of the "prompt gammas" generated by the interaction of the "burst" with the subject's tissues. Therefore, this module uses the emission point of the "prompt gammas" to reconstruct an image of the interaction volume inside which the hadrons of the "burst" interact with the tissues.

In one embodiment, the beam imaging module is furthermore configured to identify and re-eject any data corresponding to events which are not based on the interaction of a "prompt gamma" in the sensitive volume of the Compton telescope.

The system also comprises a tumour imaging module configured to receive data acquired by the Compton telescope when no "burst" impacts on the subject. In an embodiment, the data acquisition is performed on-line and continuously and only the data acquired between two successive subject "bursts" are sent to the tumour imaging module. This makes it possible to only select the data from the beta decay of the radioisotope captured by the tumour cells. This module is furthermore configured to analyse these data so as to extract the position of the tumour cells labelled with the radiopharmaceutical product by simultaneously detecting the de-excitation gamma ray and two annihilation gamma rays produced by the positron and use the position of the tumour cells to reconstruct an image of the total volume of the tumour to be treated by the hadron beam during the hadron-therapy treatment.

In one embodiment, the Compton telescope is a liquid-xenon Compton telescope.

The system further comprises an evaluation module configured to compare the image of the interaction volume and the image of the total tumour volume so as to locate the measured interaction volume relative to the measured total volume of the tumour and, each time the measured interaction volume is at least partially included in the measured total volume of the tumour, to compute the deviation between, on one hand, the position of the measured interaction volume relative to the measured total volume of the tumour and, on the other, a predefined position of the interaction volume within the total volume of the tumour defined in the treatment plan.

In one embodiment, the method evaluation module is further configured to compare the deviation between the predefined position of the interaction volume and the position of the interaction volume measured relative to the measured total volume of the tumour, to a predefined threshold.

In one embodiment, the system further comprises a correction module configured to compute at least one new parameter of the hadron beam each time the deviation is greater than the predefined threshold, in order to correct at least one characteristic of the hadron beam.

As explained in the first part of the description, the predefined parameters defining the characteristics of the hadron beam vary according to the type of hadron-therapy treatment. Based on the type of treatment that can be delivered by the treatment nozzle, the predefined parameters capable of being dynamically influenced during a session comprise the beam energy, the hadron path modulation (i.e. SOBP), the hadron path modulation and/or the X and Y position of the beam.

In one embodiment, the correction module is furthermore configured to send the new parameter of the hadron beam to the acceleration device which modifies at least one characteristic of the hadron beam so as to modify the position of the interaction volume relative to the measured total volume of the tumour.

In an embodiment, the acceleration device comprises a treatment nozzle disposed in the treatment room in a fixed position relative to the treatment table.

In an embodiment, the treatment table T is configured to move the subject relative to the point of incidence of the beam, particularly during the hadron-therapy treatment. In this first embodiment illustrated in FIG. 1, the treatment table T is capable of rotating about the three axes A1, A2 and A3 in both directions of rotation and of translating along the axes A1, A2 and A3 in both opposite directions of each axis.

In this first embodiment, the Compton telescope TC comprises two Compton semi-detectors in the form of two hollow half-cylinders, symmetrical relative to the axis A1 and separated from one another along the direction A2 so as to enable the passage of a beam F arriving above the subject. The two half-cylinders are complementary and capable of forming a full hollow cylinder if joined. Particularly, each semi-detector forms an arc of a circle having an angle 180°. In this embodiment, each Compton semi-detector is capable of translating along the axes A1, A2 and A3 in both directions and rotating about the axis A3.

In the second embodiment illustrated in FIG. 3, the treatment table T is also capable of rotating about the three axes A1, A2 and A3 in both directions of rotation and of translating along the axes A1, A2 and A3 in both opposite directions of each axis. The Compton telescope TC comprises two Compton semi-detectors in the form of two hollow half-cylinders, symmetrical relative to the axis A1 and separated from one another along the direction A3 so as to enable the passage of a beam F arriving on the subject's side.

The configuration of the Compton telescope in the first and second embodiments is referred to in the present description as "open-configuration Compton telescope". In the first and second embodiments, each Compton semi-detector can be moved independently from each other to adapt more to the position and direction of incidence of the beam F on the subject while retaining the most closed configuration possible of the Compton telescope TC on the subject. Indeed, the Compton telescope has a higher spatial resolution when the two semi-detectors are closest to the subject enabling the detection of a greater number of events (i.e. prompt gammas, de-excitation gamma ray or annihilation gamma).

In the third embodiment illustrated in FIG. 4, the Compton telescope comprises a single detection volume having the form of a hollow cylinder and comprising a lateral slit having dimensions capable of allowing the passage of a beam F arriving on the subject's side. This configuration of the Compton telescope is referred to in the present description as "closed-configuration Compton telescope". The treatment table T aligned along the axis A1, being also the longitudinal axis of a hollow cylinder. The treatment table T is capable of being moved inside the closed-configuration Compton telescope and particularly of rotating about the three axes A1, A2 and A3 in both directions of rotation and of translating along the axes A1, A2 and A3 in both opposite directions of each axis. In this embodiment, the Compton telescope is mounted on a mechanical support, motorised so as to be able to translate along the axes A1, A2 and A3 and to pivot about the axis A3.

In the first, second and third embodiments, the treatment table T whereon the subject is positioned is solidly mounted on a motorised mechanical support (not shown) which enables it to move with the degrees of freedom described hereinafter. The motorised mechanical support is particularly capable of enabling rotating movements of the treatment table T with an interval which varies between 2 and 15 degrees and translation movements by an interval which varies between 0.5 cm and 5 cm.

In one embodiment, the motorised support is a robotic positioning arm configured to have a sensitivity between 0.1 cm and 1 cm.

In the embodiments comprising a treatment table T on a motorised mechanical support, at least one of the predefined parameters of the treatment plan corresponds to the spatial position of the motorised mechanical support, particularly the treatment table T. The correction module de correction is furthermore configured to compute a new parameter of the treatment plan corresponding to a new spatial position of the motorised mechanical support so as to correct at least one characteristic of the hadron beam, corresponding particularly to the direction and point of incidence of the beam.

In the embodiments wherein the Compton telescope is capable of being moved, at least one of the predefined parameters of the treatment plan corresponds to the spatial position of the closed-configuration Compton telescope or of each Compton semi-detector of the open-configuration Compton telescope. The correction module is furthermore configured to compute a new parameter of the treatment plan corresponding to a new spatial position of the closed-configuration Compton telescope or of each Compton semi-detector of the open-configuration Compton telescope.

In one embodiment, the correction module is furthermore configured to send the new parameter of the hadron beam relating to a new position of the motorised mechanical support to the motorised mechanical support itself, so as to modify the direction and/or the point of incidence of the beam and therefore the position of the interaction volume relative to the measured total volume of the tumour.

In one embodiment, the system comprises an image reconstruction module configured to reconstruct a three-dimensional image sequence resulting from the merging of a three-dimensional image of the interaction volume with a three-dimensional image with the total tumour volume according the same Compton camera reference. This makes it possible to obtain a film of the treatment session.

In one embodiment, the modules of the system comprise at least one processor and at least one processor-readable recording medium.

The term "processor" should not be interpreted as being limited to "hardware" capable of running a software, but refers generally to a processing device, which can for example include a computer, a microprocessor, an integrated circuit or a programmable logic controller (PLD). The processor can also comprise one or more graphics processing units (GPU), whether they are used for infographics and image processing or for other functions. Furthermore, the instructions and/or the data for executing the associated and/or resulting functionalities can be stored on any medium readable by a processor such as, for example, an integrated circuit, a hard drive, a CD (Compact Disc), an optical disc such as a DVD (Digital Versatile Disc), a RAM (Random-Access Memory) or a ROM (Read-Only Memory). The instructions can particularly be stored in hardware, software, microprograms or in any combination thereof.

The invention also relates to a computer program comprising instructions which, when the program is run by a computer, result in the latter implementing the method for monitoring a hadron beam described above.

The invention also relates to a computer-readable recording medium comprising instructions which, when they are run by a computer, result in the latter implementing the method for monitoring a hadron beam described above.

In an embodiment, the computer-readable recording medium is non-transient.

The invention claimed is:

1. A method for monitoring a hadron beam during hadron-therapy treatment of a subject comprising tumour cells labelled with a radiopharmaceutical product having a radio-isotope emitting a positron and a de-excitation gamma ray in quasi-coincidence, wherein the hadron-therapy treatment is delivered according to a treatment plan comprising pre-defined parameters as a function of time in order to define at least one characteristic of the hadron beam over time during the hadron-therapy treatment, wherein the hadron beam comprises a plurality of discrete bunches of hadrons having the same acceleration phase and emitted at a predefined frequency by an acceleration device, the method comprising the following steps:
when a bunch of hadrons impacts on the subject:
detecting the prompt gammas generated by the interaction of the hadrons of the bunch of hadrons with the tissues of the subject by means of a liquid-xenon Compton
telescope;
using the prompt gammas detected to reconstruct an image of the interaction volume inside which the hadrons of the bunch of hadrons interact with the subject's tissues;
when no bunch of hadrons impacts on the subject:
extracting the position of the tumour cells labelled with the radiopharmaceutical product by simultaneously detecting the de-excitation gamma ray and two annihilation gamma rays produced by the positron by means of the Compton telescope;
reconstructing an image of the total volume of the tumour to be treated by the hadron beam during the hadron-therapy treatment;
comparing the image of the interaction volume and the image of the total volume of the tumour so as to locate the measured interaction volume relative to the measured total volume of the tumour;
each time the measured interaction volume is at least partially included in the measured total volume of the tumour, computing the deviation between, on one hand, the position of the measured interaction volume in the measured total volume of the tumour and, on the other, a predefined position of the interaction volume in the total volume of the tumour defined in the treatment plan.

2. The method according to claim 1, wherein the image of the interaction volume is obtained for each bunch of hadrons impacting on the subject.

3. The method according to claim 1, further comprising a step wherein the deviation between the predefined position of the interaction volume and the position of the interaction volume measured relative to the measured total volume of the tumour is compared to a predefined threshold.

4. The method according to claim 1, wherein, each time the deviation is greater than the predefined threshold, the method comprises a step of computing at least one new parameter of the hadron beam so as to correct at least one characteristic of the hadron beam.

5. The method according to claim 1, wherein the subject is positioned on a motorised mechanical support configured to move the subject relative to the beam during the hadron-therapy treatment and wherein at least one of the predefined parameters of the treatment plan corresponds to the spatial position of the motorised mechanical support.

6. The method according to claim 5, wherein, each time the deviation is greater than the predefined threshold, the method comprises a step of computing the parameter of the treatment plan corresponding to a new spatial position of the motorised mechanical support so as to correct at least one characteristic of the hadron beam.

7. The method according to claim 1, wherein the new parameter of the hadron beam is sent to the acceleration device, which modifies at least one characteristic of the hadron beam so as to modify the position of the interaction volume relative to the measured total volume of the tumour.

8. The method according to claim 1, wherein, each time the deviation is greater than the predefined threshold, the method comprises stopping the hadron beam.

9. The method according to claim 1, further comprising a step of reconstructing a three-dimensional image sequence resulting from the merging of a three-dimensional image of the interaction volume with a three-dimensional image with the total tumour volume in the same Compton camera reference.

10. The method according to claim 1, wherein the Compton telescope is a liquid-xenon Compton telescope.

11. A system for monitoring a hadron beam during hadron-therapy treatment of a subject comprising tumour cells labelled with a radiopharmaceutical product having a radioisotope emitting a positron and a de-excitation gamma ray in quasi-coincidence, wherein the hadron-therapy treatment is delivered according to a treatment plan comprising predefined parameters as a function of time in order to define at least one characteristic of the hadron beam over time during the hadron-therapy treatment, wherein the hadron beam comprises a plurality of discrete bunches of hadrons emitted at a predefined frequency by an acceleration device, the system comprising:

a beam imaging module configured to receive the data acquired from a liquid-xenon Compton telescope when a bunch of hadrons impacts on the subject and to analyse these data so as to determine the emission point of the prompt gammas generated by the interaction of the bunch of hadrons with the subject's tissues from which an image of the interaction volume inside which the hadrons of the bunch of hadrons interact with the tissues is reconstructed;

a tumour imaging module configured to receive the data acquired by the Compton telescope, when no bunch of hadrons impacts on the subject and to analyse these data so as to extract the position of the tumour cells labelled with the radiopharmaceutical product by simultaneously detecting the de-excitation gamma ray and two annihilation gamma rays produced by the positron and use the position of the tumour cells to reconstruct an image of the total volume of the tumour to be treated by the hadron beam during the hadron-therapy treatment; and an evaluation module configured to compare the image of the interaction volume and the image of the total tumour volume so as to locate the measured interaction volume relative to the measured total volume of the tumour and, each time the measured interaction volume is at least partially included in the measured total volume of the tumour, to compute the deviation between, on one hand, the position of the measured interaction volume relative to the measured total volume of the tumour and, on the other, a predefined position of the interaction volume within the total volume of the tumour defined in the treatment plan.

12. The system according to claim 11, wherein the evaluation module is further configured to compare the deviation between the predefined position of the interaction volume and the position of the interaction volume measured relative to the measured total volume of the tumour, to a predefined threshold.

13. The system according to claim 11, further comprising a correction module configured to compute at least one new parameter of the hadron beam, each time the deviation is greater than the predefined threshold, in order to correct at least one characteristic of the hadron beam.

14. The system according to claim 11, wherein the correction module is furthermore configured to send the new parameter of the hadron beam to the acceleration device which modifies at least one characteristic of the hadron beam so as to modify the position of the interaction volume relative to the measured total volume of the tumour.

15. The system according to claim 11, further comprising a safety module configured to send the acceleration device the instruction to stop the hadron beam each time the deviation is greater than the predefined threshold.

* * * * *